(12) United States Patent
Shen et al.

(10) Patent No.: US 8,522,602 B2
(45) Date of Patent: Sep. 3, 2013

(54) SYSTEM FOR DETECTING A LIQUID SAMPLE

(75) Inventors: Chi-Yen Shen, Kaohsiung (TW);
Ke-Nung Huang, Kaohsiung (TW);
Shen-Li Fu, Kaohsiung (TW);
Jian-Jhong Chen, Kaohsiung (TW);
Yu-Fong Huang, Kaohsiung (TW)

(73) Assignee: I Shou University, Kaohsiung (TW)

( * ) Notice: Subject to any disclaimer, the term of this patent is extended or adjusted under 35 U.S.C. 154(b) by 183 days.

(21) Appl. No.: 13/091,435

(22) Filed: Apr. 21, 2011

(65) Prior Publication Data

US 2012/0266662 A1  Oct. 25, 2012

(51) Int. Cl.
*G01N 11/00* (2006.01)
*G01N 1/00* (2006.01)

(52) U.S. Cl.
USPC ........................................ 73/53.01; 73/64.56

(58) Field of Classification Search
USPC ...... 73/61.41, 64.56, 61.48, 53.01; 422/68.1, 422/51, 52
See application file for complete search history.

(56) References Cited

U.S. PATENT DOCUMENTS 6,208,880 B1 * 3/2001 Bentsen et al. ............... 600/322

* cited by examiner

*Primary Examiner* — Daniel S. Larkin
*Assistant Examiner* — Jamar Ray
(74) *Attorney, Agent, or Firm* — Kilpatrick Townsend & Stockton LLP (57) ABSTRACT

A system is provided for detecting a liquid sample, and includes: a flow cell assembly formed with a sample receiving space therein, and inlet and outlet channels extending to the sample receiving space for guiding the liquid sample into and away from the sample receiving space; a sensor device including a sample detecting unit that is disposed in the sample receiving space, and that is operable to detect the liquid sample and to generate a detection signal accordingly, and a signal conducting unit that is connected electrically to the sensor device for conducting the detection signal therefrom; and a liquid introducing unit and a liquid discharging unit coupled to the inlet and outlet channels and cooperating therewith to form an introducing path and a discharging path for introducing the liquid sample into and for discharging the liquid sample from the sample receiving space, respectively.

8 Claims, 7 Drawing Sheets

SYSTEM FOR DETECTING A LIQUID SAMPLE

BACKGROUND OF THE INVENTION

1. Field of the Invention

The present invention relates to a system for detecting a liquid sample.

2. Description of the Related Art

As molecular biology develops rapidly in recent years, pathological variations and biological mechanisms of various diseases may now be studied and investigated at a molecular level. Moreover, prognoses of diseases may now be performed based upon subtle, molecular symptoms of the diseases.

SUMMARY OF THE INVENTION

An object of the present invention is to provide a system for detecting a liquid sample, such as a biological liquid sample.

A system for detecting a liquid sample, according to the present invention, includes:

a flow cell assembly formed with a sample receiving space therein, an inlet channel extending to the sample receiving space for guiding the liquid sample into the sample receiving space, and an outlet channel extending to the sample receiving space for guiding the liquid sample away from the sample receiving space;

a sensor device including a sample detecting unit that is disposed in the sample receiving space, and that is operable to detect the liquid sample and to generate a detection signal accordingly, and a signal conducting unit that is connected electrically to the sensor device for conducting the detection signal therefrom;

a liquid introducing unit coupled to the inlet channel and cooperating therewith to form an introducing path for introducing the liquid sample into the sample receiving space; and a liquid discharging unit coupled to the outlet channel and cooperating therewith to form a discharging path for discharging the liquid sample from the sample receiving space.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Before the present invention is described in greater detail, it should be noted that like elements are denoted by the same reference numerals throughout the disclosure.

Figure 1:
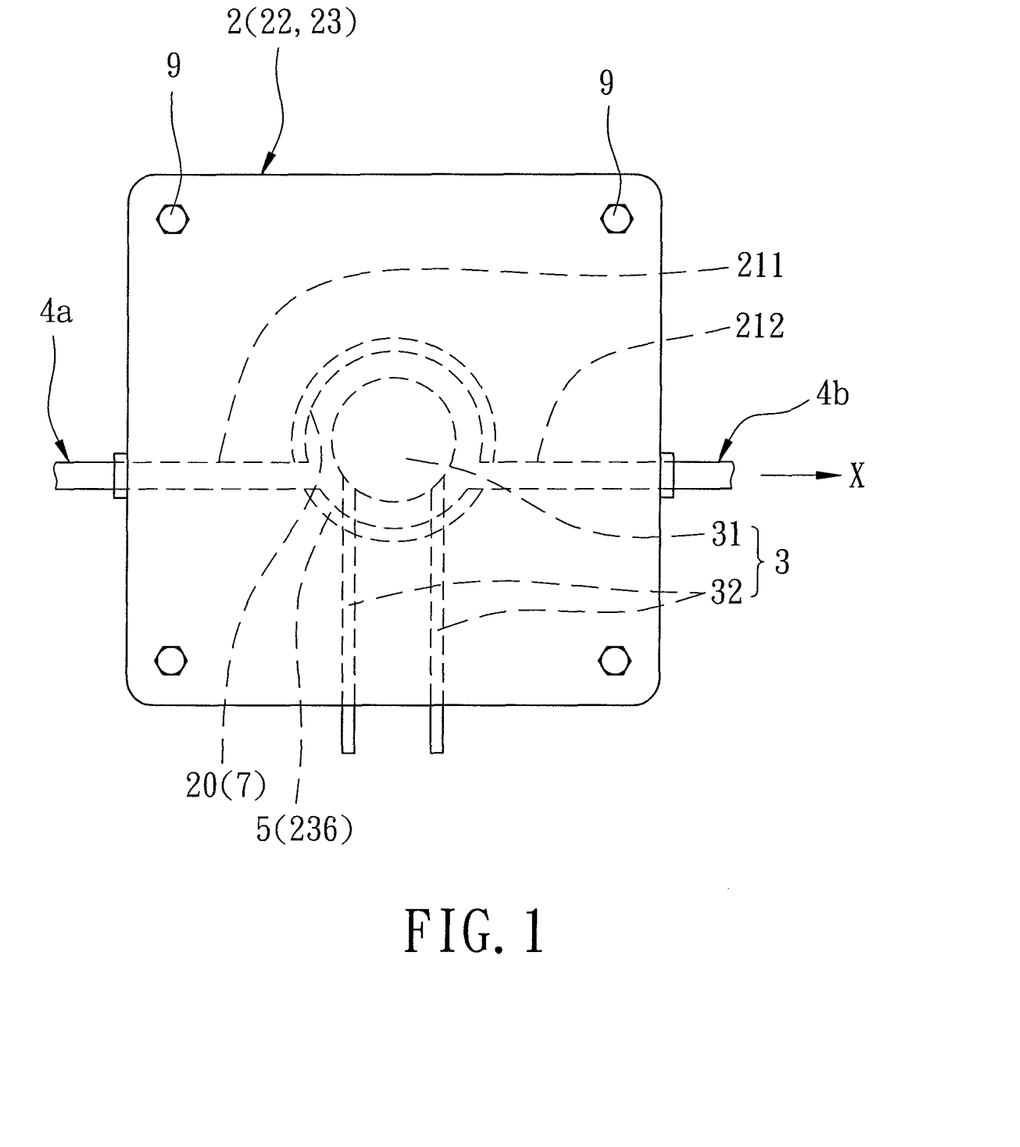
FIG. 1 is a schematic diagram of the first preferred embodiment of a system for detecting a liquid sample according to the present invention.
Figure 2:
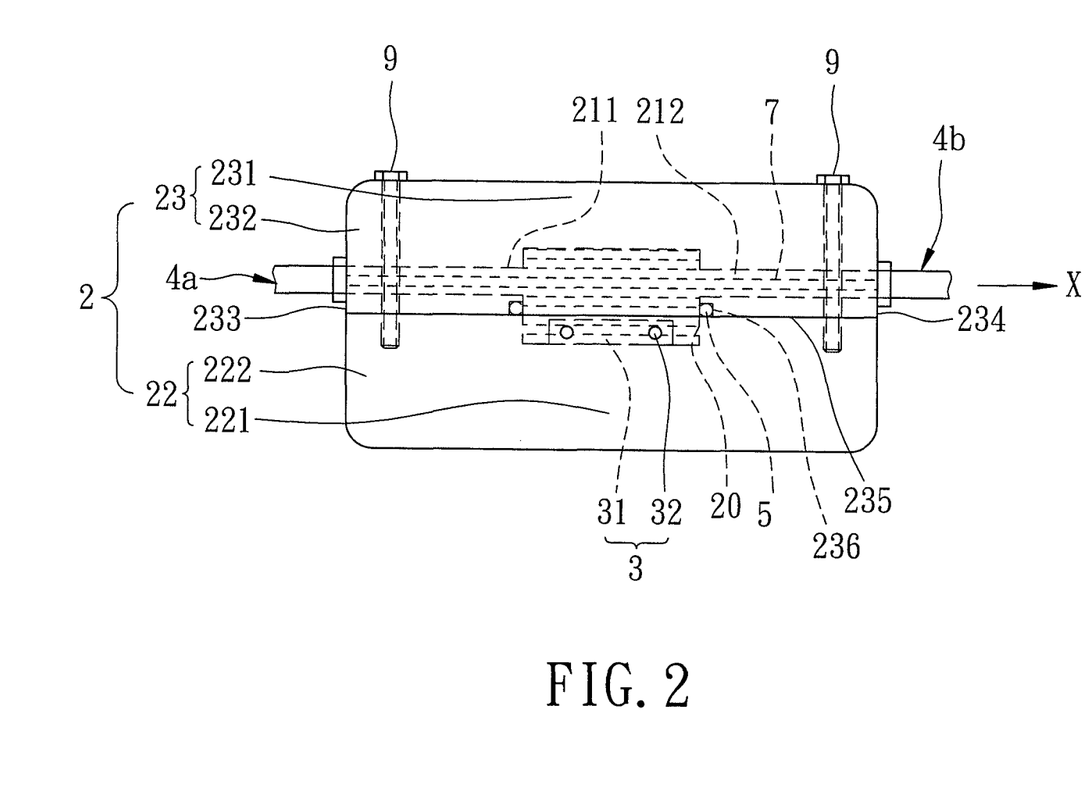
FIG. 2 is another schematic diagram of the system viewed from another angle.

Referring to FIGS. 1 and 2, the first preferred embodiment of a system for detecting a liquid sample 7, according to the present invention, includes a flow cell assembly 2, a sensor device 3, a liquid introducing unit 4a, a liquid discharging unit 4b, and a first leak-proofing ring 5.

The flow cell assembly 2 is formed with a sample receiving space 20 therein, an inlet channel 211 extending to the sample receiving space 20 for guiding the liquid sample 7 into the sample receiving space 20, and an outlet channel 212 extending to the sample receiving space 20 for guiding the liquid sample 7 away from the sample receiving space 20.

The sensor device 3 includes a sample detecting unit 31 that is disposed in the sample receiving space 20, and that is operable to detect the liquid sample 7 and to generate a detection signal accordingly, and a signal conducting unit 32 that is connected electrically to the sample detecting unit 31 for conducting the detection signal therefrom.

In the first preferred embodiment, the flow cell assembly 2 includes a base member 22, a cover member 23, and a plurality of screw fasteners 9 for fastening together the base and cover members 22, 23. The base member 22 has a base portion 221 and a first enclosure portion 222 that extends from the base portion 221 toward the cover member 23. The cover member 23 has a cover portion 231 and a second enclosure portion 232 that extends from the cover portion 231 toward the base member 22 and that abuts against the first enclosure portion 222. The second enclosure portion 232 has opposite first and second outer sides 233, 234 from which the inlet and outlet channels 211, 212 extend respectively in a substantially horizontal direction to the sample receiving space 20. Furthermore, the base and cover members 22, 23 cooperate to confine the sample receiving space 20. Such a configuration of the base and cover members 22, 23 ensures that detection of the liquid sample 7 is performed while the liquid sample 7 in the sample receiving space 20 is in a state of stable pressure.

The second enclosure portion 232 has a surface 235 that abuts against the first enclosure portion 222, and that is formed with a first recess 236 surrounding the sample receiving space 20. The first leak-proofing ring 5, which may be a rubber ring, is disposed in the first recess 236 and cooperates with the first and second enclosure portions 222, 232 so as to prevent the liquid sample 7 from leaking between the first and second enclosure portions 222, 232.

The liquid introducing unit 4a is coupled to the inlet channel 211 and cooperates therewith to form an introducing path for introducing the liquid sample 7 into the sample receiving space 20. The liquid discharging unit 4b is coupled to the outlet channel 212 and cooperates therewith to form a discharging path for discharging the liquid sample 7 from the sample receiving space 20.

In the first preferred embodiment, when the liquid sample 7, such as a biological liquid sample, flows through the sample receiving space 20, the sample detecting unit 31 is operable to detect the liquid sample 7 in a known manner and to generate the detection signal (e.g., an electrical signal) accordingly. Subsequently, the signal conducting unit 32 conducts the detection signal from the sample detecting unit 31 so as to output the detection signal for subsequent analysis. The system of the first preferred embodiment is relatively portable, easy to assemble and disassemble, customizable, and less complex in terms of structure.

Figure 3:
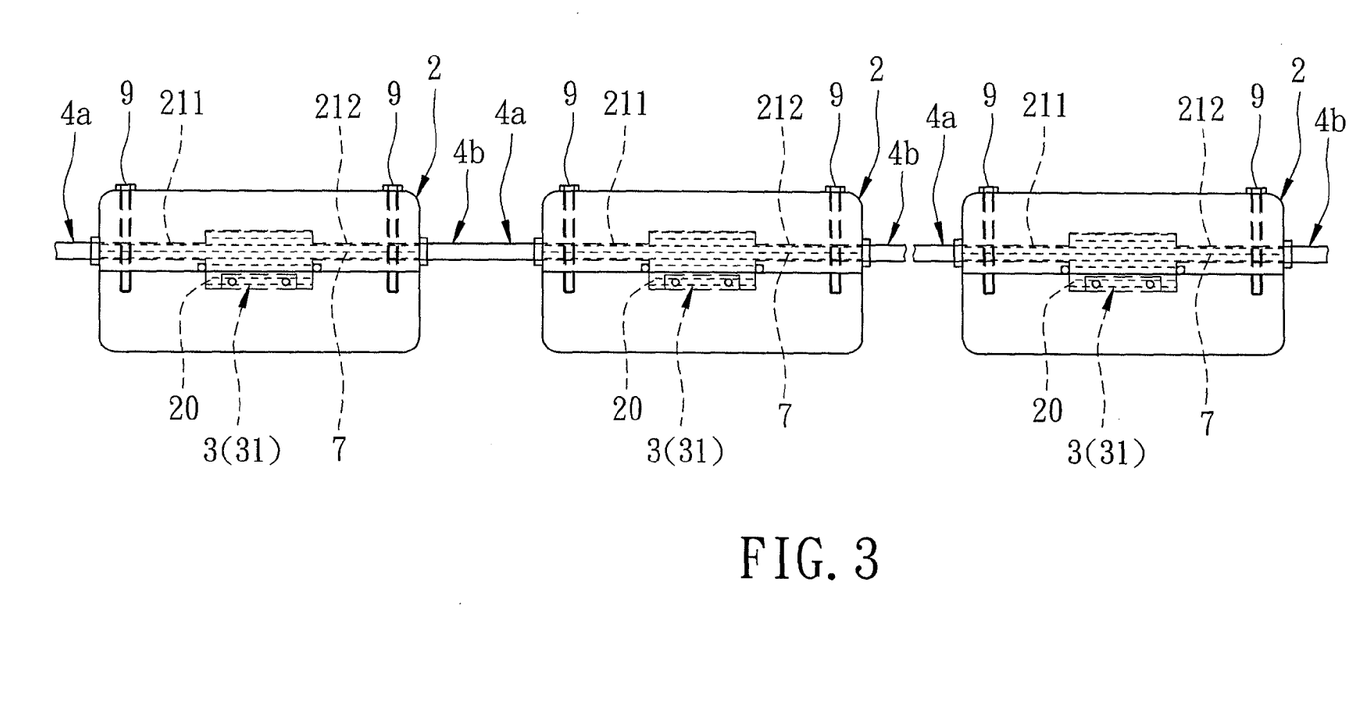
FIG. 3 is a schematic diagram of the second preferred embodiment of a system for detecting a liquid sample according to the present invention.

It is to be noted that the system of this invention may include more than one flow cell assembly 2. Referring to FIG. 3, the second preferred embodiment of a system for detecting a liquid sample, according to the present invention, includes three flow cell assemblies 2. In this embodiment, the liquid discharging unit 4b of a first one of the flow cell assemblies 2 is coupled to the liquid introducing unit 4a of an intermediate one of the flow cell assemblies 2, and the liquid discharging unit 4b of the intermediate one of the flow cell assemblies 2 is coupled to the liquid introducing unit 4a of a last one of the flow cell assemblies 2, such that the sample receiving spaces 20 of the flow cell assemblies 2 are in fluid communication with one another. Such an arrangement enables the liquid sample 7 to be introduced through the liquid introducing unit 4a of the first one of the flow cell assemblies 2, to flow through the sample receiving spaces 20 in sequence, and to be discharged through the sample discharging unit 4b of the last one of the flow cell assemblies 2.

In practice, the sample detecting units 31 of the sensor devices 3 in the sample receiving spaces 20 may be independently coated with different antibodies for capturing different antigens, which enables detection of different biomarkers in the same liquid sample 7. Furthermore, the biomarkers may correspond to the same disease or to different diseases. A result of detection thus obtained generally has a higher accuracy and hence is more reliable.

Figure 4:
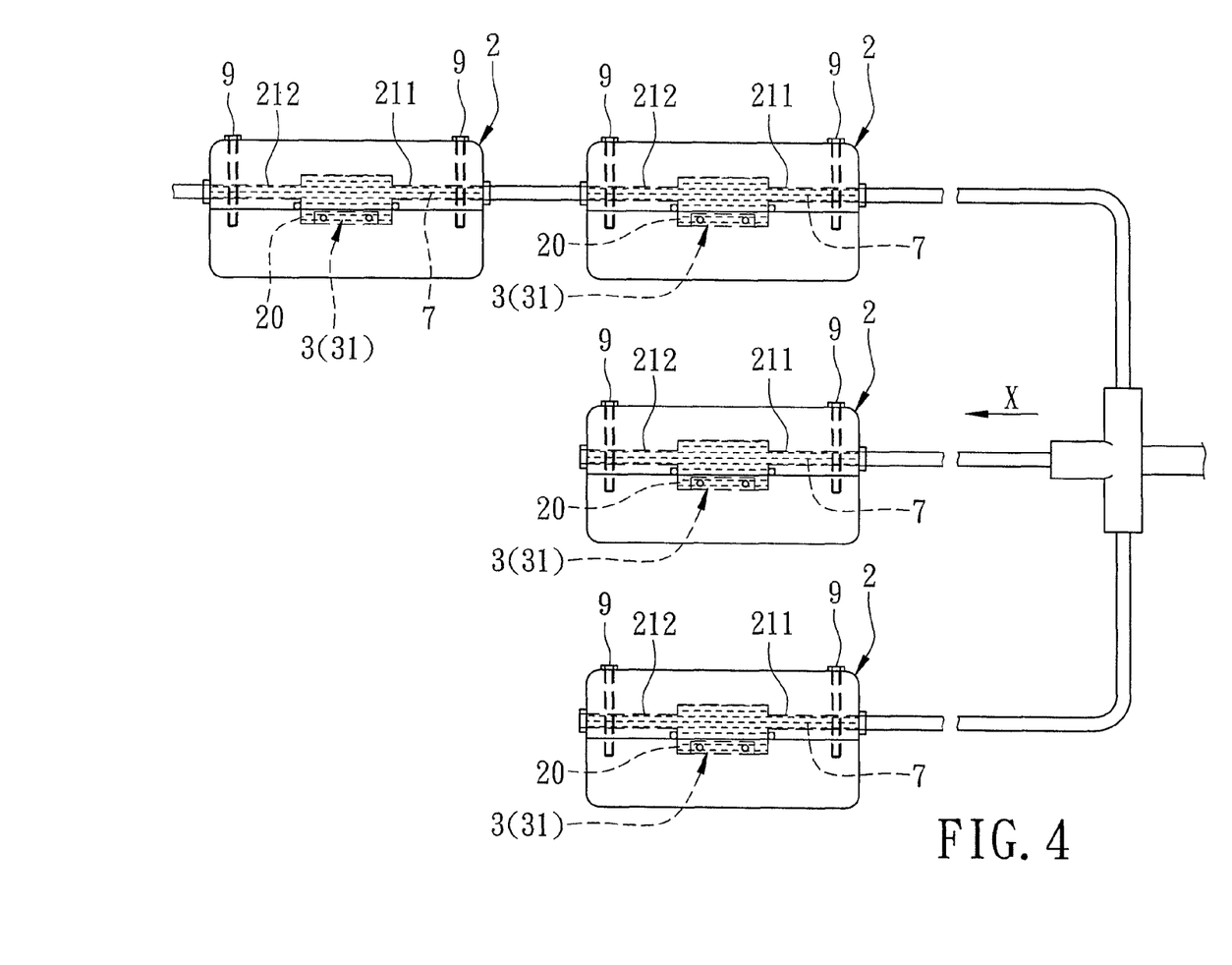
FIG. 4 is a schematic diagram of the third preferred embodiment of a system for detecting a liquid sample according to the present invention.

Configuration of the system is not limited to such. Referring to FIG. 4, the third preferred embodiment of a system for detecting a liquid sample according to the present invention has relatively a complex configuration.

In comparison with the system of the third preferred embodiment, the system of the second preferred embodiment requires a lower volume of the liquid sample 7 for obtaining an accurate result of detection.

After the liquid sample 7 has reacted with the antibody disposed on the sample detecting unit 31 of the first one of the flow cell assemblies 2, the liquid sample 7 may become contaminated such that detection accuracy of the sample detecting units 31 of remaining ones of the flow cell assemblies 2 may be compromised. The configuration of the third preferred embodiment may reduce effect of contamination of the liquid sample 7 on detection accuracy. In the third preferred embodiment, the liquid sample 7 is introduced directly into branches comprised of the flow cell assemblies 2, and a pump (not shown) may be used to drive flow of the liquid sample 7 through the flow cell assemblies 2.

Figure 5:
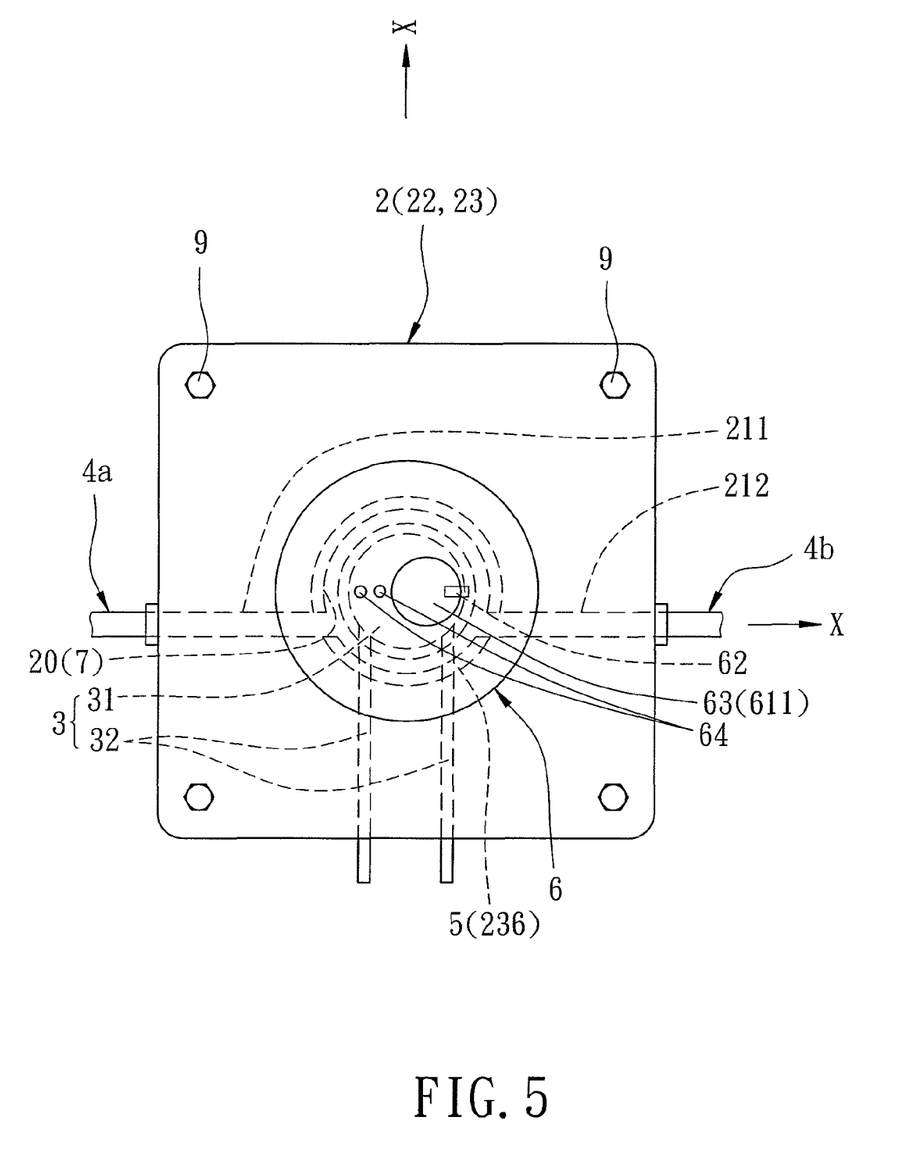
FIG. 5 is a schematic diagram of the fourth preferred embodiment of a system for detecting a liquid sample according to the present invention.
Figure 6:
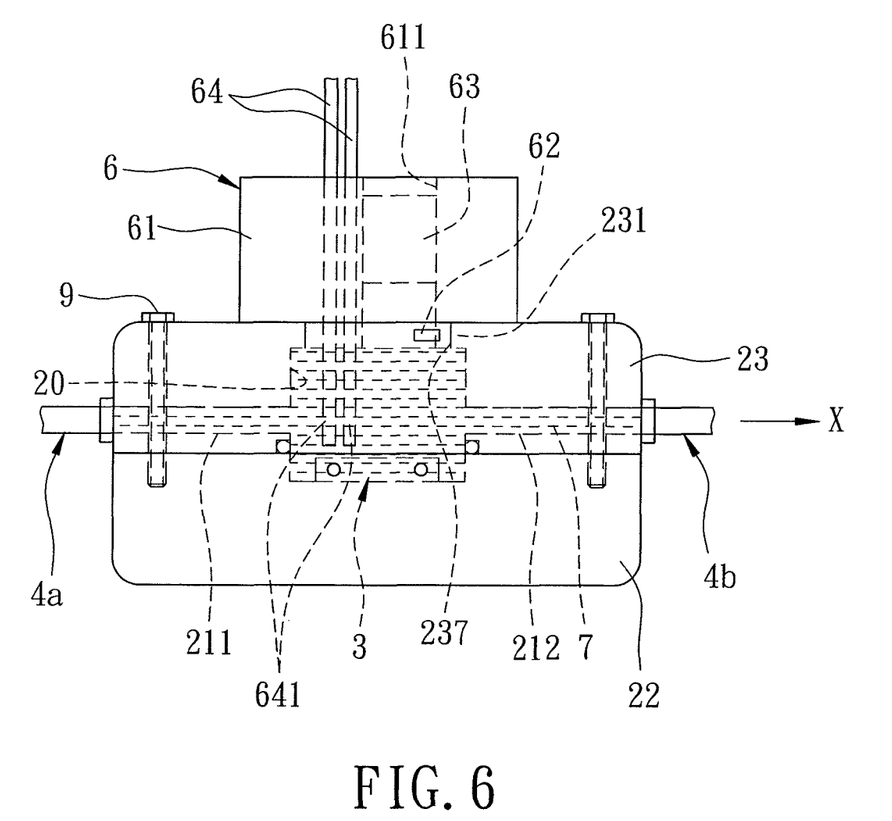
FIG. 6 is another schematic diagram of the system of the fourth preferred embodiment viewed from another angle.

Referring to FIGS. 5 and 6, the difference between the first and fourth preferred embodiments resides in that, in the fourth preferred embodiment, the cover member 23 is formed with a sample-observation channel 237 that extends to the sample receiving space 20. The system further includes a sample-observation unit 6 disposed to abut against the cover portion 231 such that the cover member 23 is interposed between the sample-observation unit 6 and the base member 22.

The sample-observation unit 6 includes a sample-observation mount 61, an illumination module 62, an image-acquisition module 63, and a set of conductive probe elements 64. The sample-observation mount 61 is mounted removably on the cover portion 231 and is formed with an extending channel 611 that is in spatial communication with the sample-observation channel 237, and that extends perpendicular to the direction in which the liquid sample 7 flows. The illumination and image-acquisition modules 62, 63 are disposed in the extending channel 611, are arranged such that the illumination module 62 is disposed closer to the sample receiving space 20 than the image-acquisition module 63, and are operable for illuminating and capturing images of the liquid sample 7 in the sample receiving space 20 through the sample-observation channel 237. The image-acquisition module 63 may be a charged coupled device (CCD) component. The illumination module 62 may be a light emitting diode (LED).

Each of the conductive probe elements 64 extends through the sample-observation mount 61 and the cover portion 231, extends perpendicular to the direction in which the liquid sample 7 flows, and has an end portion 641 that extends into the sample receiving space 20 for electrochemical signal interaction with the liquid sample 7 therein in a known manner. In this embodiment, the set of conductive probe elements 64 includes two conductive probe elements 64 that are preferably made of gold (Au) and silver (Ag), respectively.

The system of the fourth preferred embodiment is applicable to detection of a single disease. A modification of the system of the fourth preferred embodiment based on the second preferred embodiment is applicable to detection of multiple diseases. Moreover, the liquid sample 7 in each of the sample receiving spaces 20 may be observed through the use of the sample-observation unit 6, and electrochemical signal interaction may be performed upon the liquid sample 7 in each of the sample receiving spaces 20 through the use of the conductive probe elements 64.

Figure 7:
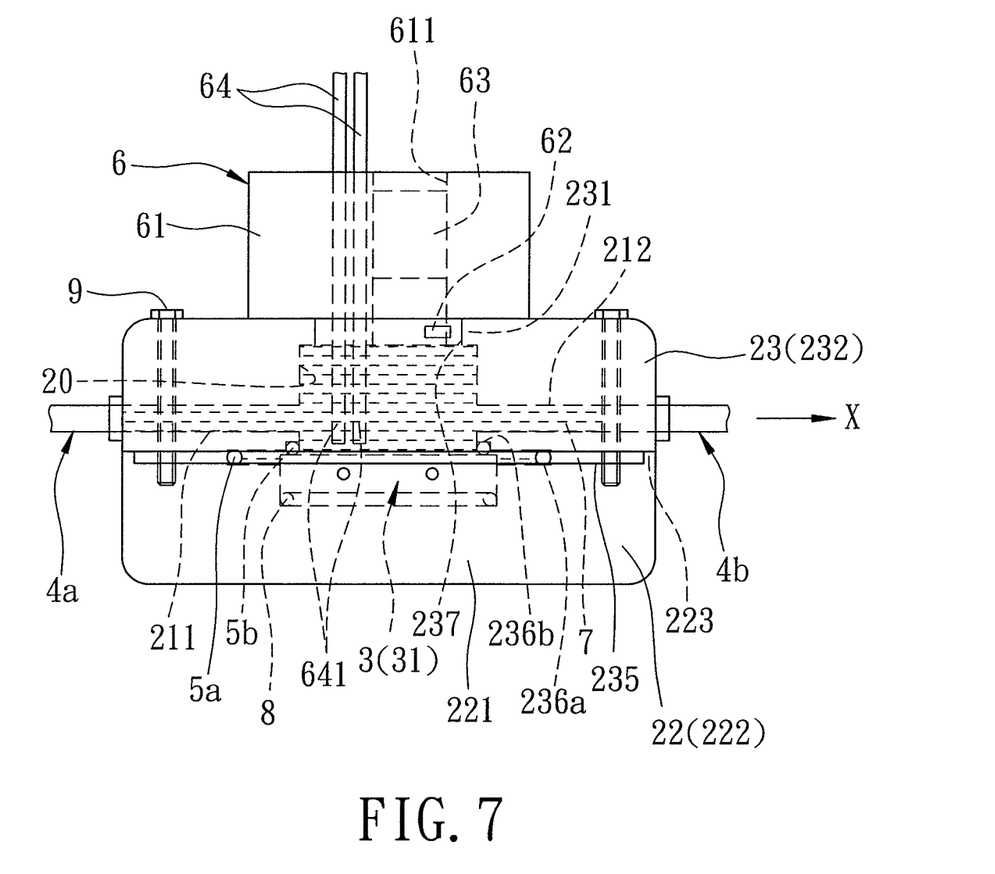
FIG. 7 is a schematic diagram of the fifth preferred embodiment of a system for detecting a liquid sample according to the present invention.

Referring to FIG. 7, the difference between the fourth and fifth preferred embodiments resides in that, in the fifth preferred embodiment, the first recess 236a has a recess bottom formed with a second recess 236b that surrounds the sample receiving space 20. The first enclosure portion 222 has a surface that abuts against the surface 235 of the second enclosure portion 232 and that confines a cavity, which forms a part of the sample receiving space 20. In addition to the first leak-proofing ring 5a, which is disposed in the first recess 236a, the system further includes a second leak-proofing ring 5b disposed in the second recess 236b, and a shock-absorbing piece 8 disposed in the cavity. The sample detecting unit 31 is interposed in the sample receiving space 20 between the second leak-proofing ring 5b and the shock-absorbing piece 8. In this embodiment, the surface of the first enclosure portion 222 is formed with a male engaging part, and the surface 235 of the second enclosure portion 232 is formed with a female engaging part. The male engaging part engages the female engaging part to limit pressure applied on the sample detecting unit 31 by the second leak-proofing ring 236b and the shock-absorbing piece 8. The male engaging part is preferably a flange 223 protruding from a periphery of the surface of the first enclosure portion 222, and the female engaging part is preferably a groove formed in the surface 235 of the second enclosure portion 232.

In summary, the preferred embodiments of a system for detecting a liquid sample, according to the present invention, are relatively portable, easy to assemble and disassemble, and customizable to meet user needs. In addition, the sample-observation unit 6 is operable for capturing images of the liquid sample 7 and for electrochemical signal interaction with the liquid sample 7. Furthermore, the system may include a plurality of flow cell assemblies 2 that are coupled together and operable for detection of a single disease or multiple diseases.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A system for detecting a liquid sample, said system comprising:
a flow cell assembly formed with a sample receiving space therein, an inlet channel extending to said sample receiving space for guiding a liquid sample into said sample receiving space, and an outlet channel extending to said sample receiving space for guiding the liquid sample away from said sample receiving space;
a sensor device including a sample detecting unit that is disposed in said sample receiving space, and that is operable to detect the liquid sample and to generate a detection signal accordingly, and a signal conducting unit that is connected electrically to said sample detecting unit for conducting the detection signal therefrom;
wherein said flow cell assembly comprises a base member and a cover member that cooperate to confine said sample receiving space, said base member having a base portion and a first enclosure portion that extends from said base portion toward said cover member, said cover member having a cover portion and a second enclosure portion that extends from said cover portion toward said base member and that abuts against said first enclosure portion, said second enclosure portion having opposite first and second outer sides from which said inlet and outlet channels extend respectively to said sample receiving space;
wherein said second enclosure portion has a surface that abuts against said first enclosure portion, and is formed with a first recess surrounding said sample receiving space, further wherein a first leak-proofing ring is disposed in said first recess and cooperates with said first and second enclosure portions so as to prevent the liquid sample from leaking between said first and second enclosure portions;
wherein said first recess has a recess bottom formed with a second recess, said second recess surrounding said sample receiving space, wherein said first enclosure portion having a surface that abuts against said surface of said second enclosure portion confines a cavity, said cavity forming a part of said sample receiving space, a second leak-proofing ring disposed in said second recess, and a shock-absorbing piece disposed in said cavity, and wherein said sample detecting unit is interposed in said sample receiving space between said second leak-proofing ring and said shock-absorbing piece;
a liquid introducing unit coupled to said inlet channel and cooperating therewith to form an introducing path for introducing the liquid sample into said sample receiving space; and
a liquid discharging unit coupled to said outlet channel and cooperating therewith to form a discharging path for discharging the liquid sample from said sample receiving space.

2. The system as claimed in claim 1, wherein one of said surface of said first enclosure portion and said surface of said second enclosure portion is formed with a male engaging part, and the other of said surface of said first enclosure portion and said surface of said second enclosure portion is formed with a female engaging part, said male engaging part engaging said female engaging part to limit pressure applied on said sample detecting unit by said second leak-proofing ring and said shock-absorbing piece.

3. The system as claimed in claim 2, wherein said male engaging part is a flange protruding from a periphery of said surface of said first enclosure portion, and said female engaging part is a groove formed in said surface of said second enclosure portion.

4. The system as claimed in claim 1, wherein said cover portion of said cover member is formed with a sample-observation channel that extends to said sample receiving space; said system further comprising a sample-observation unit disposed to abut against said cover portion such that said cover member is interposed between said sample-observation unit and said base member; said sample-observation unit including an illumination module and an image-acquisition module for illuminating and capturing images of the liquid sample in said sample receiving space through said sample-observation channel.

5. The system as claimed in claim 4, wherein said sample-observation unit further includes a sample-observation mount mounted removably on said cover portion and formed with an extending channel that is in spatial communication with said sample-observation channel, said illumination module and said image-acquisition module being disposed in said extending channel and being arranged such that said illumination module is disposed closer to said sample receiving space than said image-acquisition module.

6. The system as claimed in claim 4, wherein said sample-observation unit further includes a set of conductive probe elements extending through said sample-observation mount and said cover portion, and extending into said sample receiving space for electrochemical signal interaction with the liquid sample in said sample receiving space.

7. The system as claimed in claim 1, wherein said flow cell assembly further includes screw fasteners for fastening together said cover and base members.

8. The system as claimed in claim 1, wherein each of said inlet and outlet channels extends in a substantially horizontal direction.

* * * * *